United States Patent [19]

Albrecht et al.

[11] Patent Number: 4,747,117
[45] Date of Patent: May 24, 1988

[54] DEVICE FOR DETERMINING LOCAL ABSORPTION VALUES IN A SLICE OF A BODY, AND AN ARRAY OF DETECTORS FOR SUCH A DEVICE

[75] Inventors: Cornelis B. J. D. Albrecht; Roland A. J. O. Van Witteveen; Frans W. Zonneveld, all of Eindhoven, Netherlands

[73] Assignee: U.S. Philips Corp., New York, N.Y.

[21] Appl. No.: 63,738

[22] Filed: Jun. 17, 1987

Related U.S. Application Data

[63] Continuation of Ser. No. 898,790, Aug. 18, 1986, abandoned, which is a continuation of Ser. No. 123,638, Feb. 22, 1980, abandoned, which is a continuation of Ser. No. 948,282, Oct. 3, 1978, abandoned.

[30] Foreign Application Priority Data

Oct. 11, 1977 [NL] Netherlands ............. 7711120

[51] Int. Cl.$^4$ ............................................. H05G 1/60
[52] U.S. Cl. ........................................ 378/019; 378/4; 250/366
[58] Field of Search ............. 378/19, 4; 250/366, 250/369, 385

[56] References Cited

U.S. PATENT DOCUMENTS 4,031,396 6/1977 Whitten ..................... 378/19
4,504,962 3/1985 Moore ........................ 378/19

Primary Examiner—Carolyn E. Fields
Assistant Examiner—T. N. Grigsby
Attorney, Agent, or Firm—William L. Botjer

[57] ABSTRACT

An X-ray examining device for transversal tomography, comprising an array of detectors of mutually different dimensions. Each detector comprises one or more detector elements which operate electrically in parallel, either as a result of the direct parallel connection of the detector elements or by the addition of output signals of integrators which are connected to each detector element. It is possible to connect more or fewer detector elements in parallel by means of switches, so that it is possible to select the resolution of the array of detectors.

10 Claims, 2 Drawing Sheets

DEVICE FOR DETERMINING LOCAL ABSORPTION VALUES IN A SLICE OF A BODY, AND AN ARRAY OF DETECTORS FOR SUCH A DEVICE

This is a continuation of 898,790, filed on Aug. 18, 1986, which is a continuation of application Ser. No. 123,638, filed Feb. 22, 1980, which is a continuation of Ser. No. 948,282, filed Oct. 3, 1978, all abandoned.

BACKGROUND OF THE INVENTION

Device for determining local absorption values in a slice of a body, and an array of detectors for such a device.

The invention relates to a device for determining local radiation absorption values in a slice of a body, comprising at least one radiation source for generating a fan-shaped beam of radiation which irradiates the body, and an array of detectors for detecting radiation which passes through the body in various directions, the direction of the radiation being situated in the slice, the radiation source and the array of detectors being situated opposite each other on each side of a central axis through the body to be examined, the detectors on and near a connecting line between radiation source, central axis and array of detectors having a smaller detection surface area than the detectors which are situated further from the connecting line, a detector signal from a detector being electrically isolated from the detector signal from any other detector. The invention furthermore relates to an array of detectors for such a device.

A device of the described kind is known from U.S. Pat. No. 3,973,128. This patent describes a detector construction which has a spatial resolution, in the absorption distribution of the irradiated slice to be reconstructed, which is position-dependent. The detector construction comprises detectors whose detection surface areas facing the body are not equal. At the ends of the array of detectors, the detection surface areas are larger than the detection surface areas in the center of the array, with the result that the spatial resolution in the center of the reconstructed absorption distribution is higher than that at the edge.

SUMMARY OF THE INVENTION

An object of the invention is to provide a device in which the area of the detection surfaces of the detectors (i.e. the spatial resolution in the ultimate reconstruction of the absorption distribution) can be adapted to the nature of the body to be examined.

To this end, the device according to the invention is characterized in that the array of detectors comprises, viewed in the direction of the array, a series of consecutively arranged detector elements which have uniform dimensions and behavior. The detection surface area of a detector, made up of one or more detector elements, is therefore proportional to an integral multiple of the detection surface area of a detector element. The detector signal is proportional to the sum of the output signals of the detector elements comprising the detector.

Because all detector elements are uniform, the manufacture of an array of detectors consisting of such detector elements will be cheaper than the manufacture of an array of detectors having unequal detection surface areas.

The parallel operation of the detector elements need not be permanent. As a result, groups of detector elements can operate in parallel according to the nature of the body to be examined and the required quality of the image of the slice of the body to be examined. It has been found that this is an attractive feature, because for examinations performed on the human torso the required resolution may usually be lower than that required, for example, for basicranial examinations.

The use of an array of detectors having different dimensions creates problems, notably when ionization chambers are used as detectors. Ionization chambers of different dimensions have different response times and non-linearity. This makes calibration and processing of the detector signals difficult.

To this end, a preferred embodiment of a device according to the invention is characterized in that the detector elements are ionization chambers. The construction of detectors having unequal detection surface areas from one or more ionization chambers, each of which has a uniform behavior, results in each detector having the same response time and non-linearity, which is advantageous for the necessary calibration of the array of detectors.

In a further embodiment of the device according to the invention, the outputs of the ionization chambers associated with a detector are interconnected via electrically conductive connection means. The signal supplied by the detector is the sum of the ionization currents of the individual, parallelly connected ionization chambers. A known pre-amplifier which acts as an integrator may be connected to the parallel connection of the ionization chambers.

Another preferred embodiment of the device according to the invention is characterized in that each detector element is connected to an integrator, there being provided per detector an adding circuit whereto outputs of the integrators of the ionization chambers associated with the detector are connected via electrical connection means. In this embodiment, the connection means are preferably constructed as switches. Such a set-up of the electrical circuit connected to the detector elements offers the advantage that the susceptibility to interference is less in comparison with a construction in which switches are directly connected to the ionization chambers. Because the ionization currents have already been integrated before they are applied to an adding circuit via switches, the circuit is less susceptible to the electrical irregularities formed by the switches therein. An array of detectors, which is composed of a series of uniform ionization chambers and in which the spatial resolution is changed by the switching of switches, is attractive notably where many different kinds of examinations are performed. For example, the device according to the invention can be used to examine part of the slice to be examined with a high spatial resolution, while the surrounding parts are examined with a lower spatial resolution. Furthermore, the same device can be used to examine the entire slice with a low resolution (for example, during X-ray examination of large organs, such as lungs or liver) or with a high resolution (for example, basicranial X-ray examinations).

BRIEF DESCRIPTION OF THE DRAWING

The invention will be described in detail hereinafter with reference to the accompanying diagrammatic drawing.

FIG. 4 is a schematic diagram of another embodiment of the invention.

DESCRIPTION OF THE PREFERRED EMBODIMENTS

Figure 1:
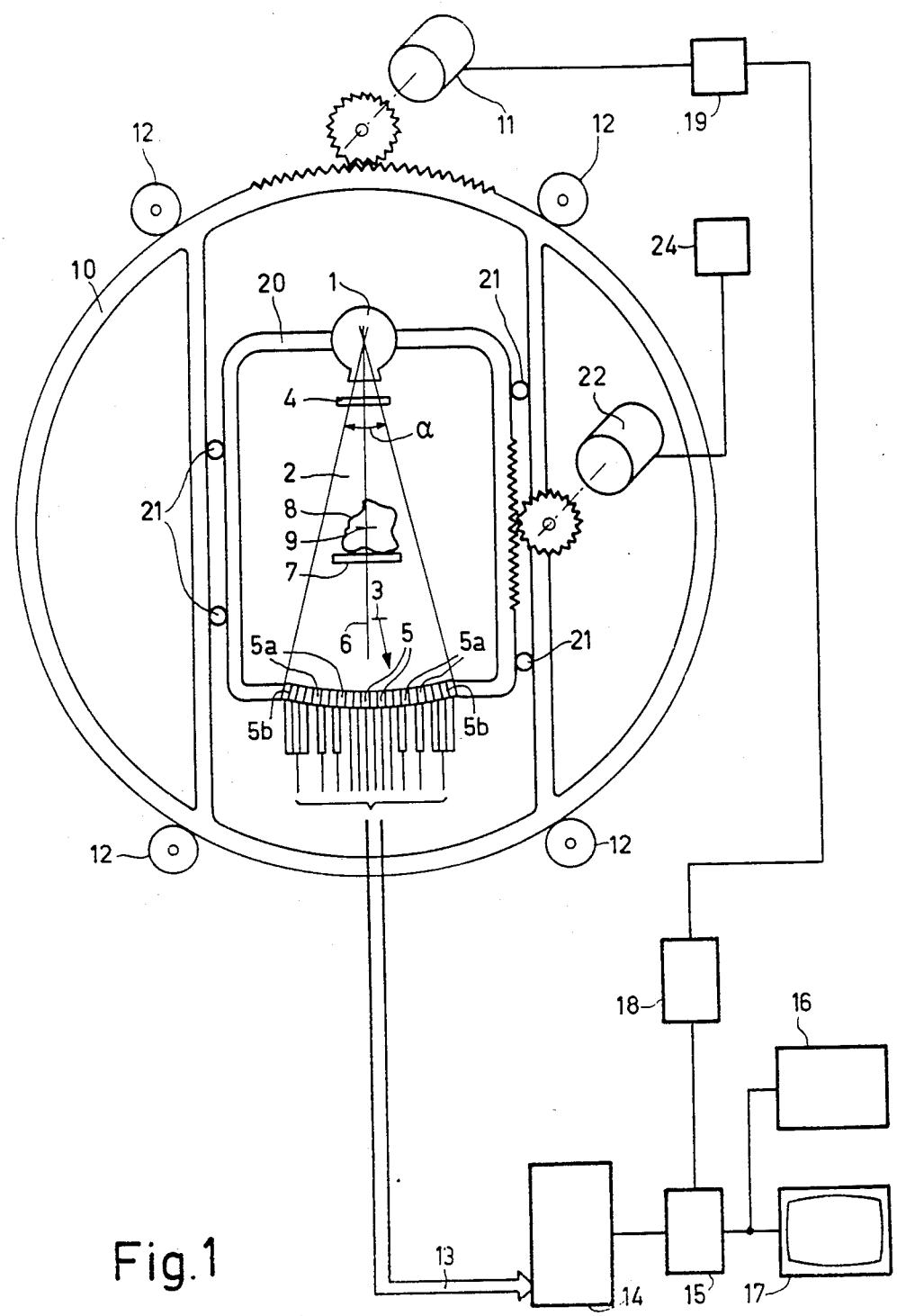
FIG. 1 shows a device according to the invention.

FIG. 1 diagrammatically shows an X-ray examining device according to the invention, comprising a radiation source 1 which preferably consists of an X-ray tube, but which may alternatively consist of, for example, a radioactive isotope such as Am241 or Gd153. An array of detectors 3 (for example, comprising 300 detectors) locally measures the intensity of the beam of radiation 2 to be emitted by the radiation source. Radiation 2 is preferably X-radiation. The radiation source in this case forms a fan-shaped beam having an angle of aperture $\alpha$ which amounts to, for example, 60°. The beam is substantially in planes parallel to the plane of the drawing and has a small thickness of, for example, from 3 to 15 mm perpendicular to the plane of the drawing. A slit-like aperture 4 is provided for the formation of such a beam. The width dimension of the detectors 3 and the distance therebetween determine the feasible spatial resolution within a given beam angle of the fan-shaped beam 2. A supporting table 7, on which a body 8 to be examined is arranged, is longitudinally displaceable along a central axis 9 which is directed perpendicularly to the plane of the drawing. The system formed by the X-ray source 1 and the array of detectors 3 can be rotated around the body 8 by means of a toothed ring 10 which is driven by a motor 11 and which is supported by guides 12. Rotation of the system formed by the X-ray source 1 and the array of detectors 3 may be continuous as well as intermittent. In the latter case a rotation step is formed after each measurement. A counter 18 counts the number of detector signals received per measurement by an arithmetic device 15. When a number is reached which corresponds to the number of detectors, the control circuit 19 of the motor 11 is actuated for a brief period of time, so that a rotation step takes place. The system formed by the X-ray source 1 and the array of detectors 3 is suspended in a frame 20. The frame 20 is movable along guide rollers 21 by means of a motor 22, so that the X-ray source 1 can be moved away from or towards the body along a central connecting line 6. It is thus achieved that the beam 2 generated by the X-ray source 1, having an apex $\alpha$, can always exactly cover the body 8, so that optimum use is made of the array of detectors 3 during the examination. Prior to the start of a measurement, the distance between the X-ray source 1 and the body 8 is adjusted, for example, by switching on the control circuit 24 by hand.

Each of the detectors 5, 5a and 5b is connected, via a cable bundle 13, to an amplifier/converter 14 in which the detector signals are individually processed. The amplifier/converter 14 may comprise, for example, a multiplex circuit and an analog-to-digital converter. The output of the amplifier/converter 14 is connected to an arithmetic device 15, whereby the local absorption is calculated on the basis of the amplified and converted detector signals. The calculated absorption values are stored in a memory device 16 and, if desired, displayed on a display device 17.

The array of detectors 3 according to the invention consists of an array of adjacently arranged detector elements which have uniform dimensions and behavior. Preferably, the detector elements are ionization chambers filled with a rare gas, such as xenon, and an extinction gas. The ionization chambers are accommodated, for example, in a gastight housing and are formed by plate-shaped, parallelly arranged, electrically conductive electrodes as have been proposed in U.S. patent application Ser. No. 895,706, filed Apr. 12, 1978 and assigned to the assignee of the instant application. The detectors 5, situated around the central connecting line 6 in the center of the X-ray beam 2, comprise, for example, one ionization chamber. Some detectors 5a which are situated on either side of detectors 5 each comprise two parallelly connected ionization chambers. Each of the detectors 5b situated at the ends of the array comprises four parallelly connected ionization chambers. If the array of detectors 3 comprises, for example, 384 ionization chambers and the angle of aperture is 48°, a practical construction of the detectors is as follows: On either side of the central connecting line 6 from 0°–15°: 8 detectors per degree (1 ionization chamber per detector)

15°–18°: 4 detectors per degree (2 ionization chambers per detector)

18°–21°: 2 detectors per degree (4 ionization chambers per detector)

21°–24°: 1 detector per degree (8 ionization chambers per detector)

The total number of detectors then amounts to 282, while the total number of ionization chambers amounts to 384.

Figure 2:
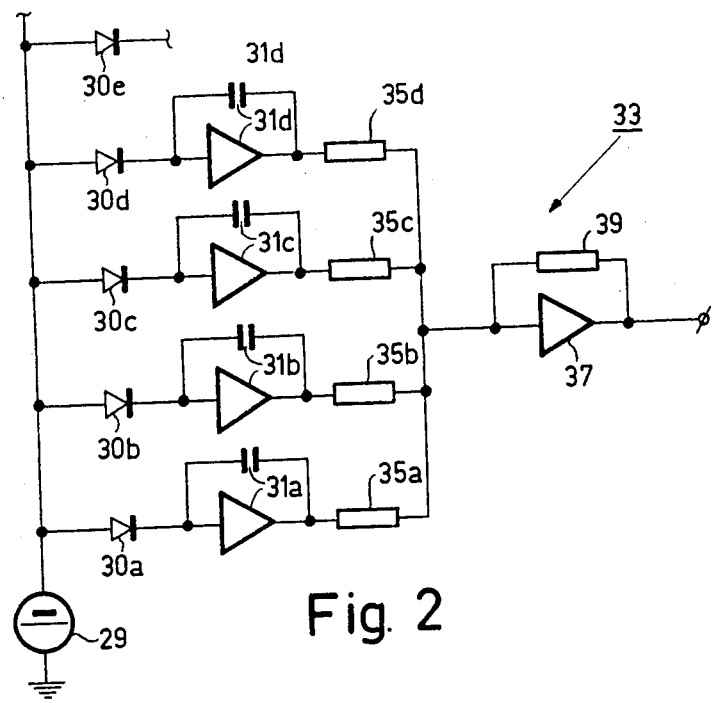
FIG. 2 shows a preferred embodiment of a part of a schematic diagram of a series of ionization chambers for a device as shown in FIG. 1.

The signal-carrying electrodes of the ionization chambers (i.e. the output signals of the detector elements) associated with a detector can be readily interconnected electrically. A further possibility of realizing parallel operation of detector elements is shown in FIG. 2. The detector elements to be used have been proposed in U.S. patent application Ser. No. 885,670, filed Mar. 13, 1978 and assigned to the assignee of the instant application. A series of detector elements 30a ... e, each of which comprises a semiconductor diode, is connected to a power supply source 29. The detector elements 30a ... e shown form only a fraction of the number of detector elements used. Each of the detector elements 30a ... d, together constituting a detector, is connected to an integrator 31a ... d which, by way of illustration, comprises an operational amplifier and a capacitor. The outputs of the integrators 31a ... d are connected to an adding circuit 33. The adding circuit 33 comprises, for example, input resistors 35a ... d which all have the same resistance, an operational amplifier 37, and a feedback resistor 39. The output signal of the adding circuit 33 is the detector signal of a detector which comprises four detector elements operating in parallel. Depending on the position of a detector in the array of detectors 3, 1, 2, 4 or 8 detector elements are connected to an adding circuit.

Figure 3:
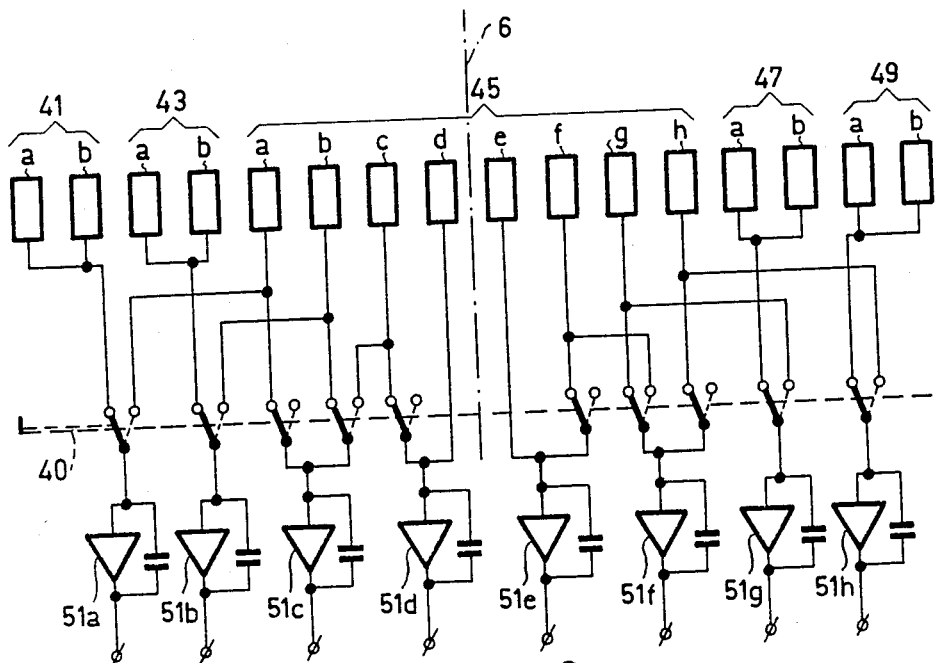
FIG. 3 shows a further embodiment of a schematic diagram of a series of detector elements for a device as shown in FIG. 1.

FIG. 3 shows a schematic diagram for a series of ionization chambers 41a, b; 43a, b; 45a ... h; 47a, b and 49a, b for a device according to the invention. FIG. 3 only shows a number of ionization chambers (16) which is small in comparison with the often more than 300 ionization chambers used in practice. The a-sections and the b-sections of the ionization chambers 41a, b; 43a, b;

47a, b and 49a, b are permanently connected in parallel and form four detectors. The ionization chambers are symmetrically arranged with respect to the central connecting line 6 which is also shown in FIG. 1. By means of a two-position switch 40, the ionization chambers can be connected to the integrators 51a . . . h in two ways. In the position of the switch 40 shown, the ionization chambers 45a and b form a detector which is connected to the integrator 51c. Each of the ionization chambers 45c and d, e and f, g and h also forms a detector which is connected to the integrators 51d, e and f, respectively. The array of detectors thus comprises 8 detectors, each of which comprises two parallelly connected ionization chambers.

When the switch 40 is switched over, the ionization chambers 45a, b, c, d, e, f, g and h are connected to the integrators 51a, b, c, d, e, f, g and h, respectively. The array of detectors in this configuration comprises 8 detectors, each of which comprises one ionization chamber. Therefore, switching over can be used to make a choice between a long array of detectors (low resolution) and a short array of detectors (high resolution), the number of detectors being the same in both arrays. The short array of detectors will enclose a smaller angle $\alpha$ (see FIG. 1) than a long array of detectors. The apex $\alpha$ of the radiation beam 2 can be adapted to the length of the array of detectors 3 by using the appropriate apertures 4.

In FIG. 3, the switch 40 is connected directly to the detector elements (ionization chambers). Obviously, it is alternatively possible to connect an integrator 51 to each detector element (as in FIG. 2) and to connect a switch 40 to the outputs thereof in order to establish and interrupt the desired connections between the outputs of the integrators and the adding circuits. (FIG. 4.) Obviously, the resistor of the adding circuit may also be permanently connected to each output of the integrators, a switch such as the switch 40 being connected to said resistors in order to establish the desired connections to the remainder of the adding circuits.

What is claimed is:

1. A device for determining local radiation absorption values in a slice of a body having a central axis, comprising:
    at least one radiation source for generating a fan-shaped beam of radiation which irradiates the slice of the body and which passes through the slice in different directions, said radiation source being situated on a first side of the central axis;
    an array of detector elements, having uniform dimensions and behavior, for detecting the radiation emitted by the radiation source, said array being situated on a second side of the central axis opposite said radiation source, each of said detector elements generating an output signal;
    means connected to the output signal from each detector element for separately time-integrating the output signals from each detector element;
    means for adding the integrated output signals from a group of detector elements, the sum being an integrated detector signal which is electrically isolated from the integrated detector signal of any other detector element or group of detector elements; and
    switchable means for connecting the integrated output signals from at least two groups of detector elements to the adding means, said switchable means connecting the integrated output signals of only one group of detector elements at a time.

2. An array of detector elements, comprising:
    a series of ionization chambers having uniform dimensions and behavior, each of said ionization chambers generating an output signal;
    means for adding the output signals from a group of one or more ionization chambers, the sum being a detector signal which is electrically isolated from the detector signal of any other ionization chamber or group of ionization chambers; and
    switchable means for connecting the output signals from at least two groups of ionization chambers to the adding means, said switchable means connecting the output signals of only one group of ionization chambers at a time.

3. An array of detector elements as claimed in claim 2, further including means for time-integrating each output signal, and wherein the switchable means connects the integrated output signals to the adding means.

4. A computerized tomography method comprising the steps of providing a plurality of detector devices arranged to measure radiation at different locations distributed around a patient position, projecting a substantially planar, fan-shaped distribution of x-radiation through a sectional slice of the body of a patient, disposed at said patient position, from many different positions distributed angularly around said patient position, causing said detector devices to provide electrical output signals indicative of the radiation emerging from said slice of the body of a patient along a plurality of mutually divergent directions from each of said positions, providing a processor, and selectively passing, to said processor, individual electrical output signals provided by individual detector devices or combination electrical signals generated by combining the electrical output signals provided by respective groups of neighboring detector devices, the numbers of devices in such groups being selectable, and causing said processor to process the signals selectively passed to the processor to generate, in part from said electrical output signals or combination electrical signals selectively passed thereto, electrical data signals indicative of the attenuation suffered by the x-radiation passing through the slice along various directions and to generate, in part from said electrical data signals, a representation of the variation of an x-ray response characteristic over said slice.

5. A device for determining local radiation absorption values in a slice of a body having a central axis, said device comprising:
    at least one radiation source for generating a fan-shaped beam of radiation which irradiates the slice of the body and which passes through the slice in different directions, said radiation source being situated on a first side of the central axis;
    an array of detector elements, having uniform dimensions and behavior, for detecting the radiation emitted by the radiation source, said array being situated on a second side of the central axis opposite said radiation source, each of said detector elements generating an output signal;
    means for forming group output signals as either individual detector element output signals or as combination output signals formed by combining the output signals of two or more neighboring detector elements; and
    means for selecting the number of detector elements whose output signals form group output signals.

6. A device for determining local radiation absorption values in a slice of a body having a central axis, comprising:
- at least one radiation source for generating a fan-shaped beam of radiation which irradiates the slice of the body and which passes through the slice in different directions, said radiation source being situated on a first side of the central axis;
- an array of detector elements, having uniform dimensions and behaviour, for detecting the radiation emitted by the radiation source, said array being situated on a second side of the central axis opposite said radiation source, each of said detector elements generating an output signal;
- means for adding the output signals from a group of one or more detector elements, the sum being a detector signal which is electrically isolated from the detector signal of any other detector element or group of detector elements;
- means connected to the detector signal for time-integrating the detector signal; and
- switchable means for connecting the output signals from at least two groups of one or more detector elements to the adding means, said switchable means connecting the output signals of only one group of detector elements at a time.

7. A device as claimed in claim 6, wherein the detector elements are ionization chambers.

8. A device as claimed in claim 7, wherein the groups of detector elements which are on and near a connecting line between the radiation source, central axis and array of detector elements are smaller than the groups of detector elements which are situated farther from the connecting line.

9. A device as claimed in claim 1, wherein the detector elements are ionization chambers.

10. A device as claimed in claim 9, wherein the groups of detector elements which are on and near a connecting line between the radiation source, central axis and array of detector elements are smaller than the groups of detector elements which are situated farther from the connecting line.

* * * * *